United States Patent
King et al.

(10) Patent No.: US 11,331,467 B2
(45) Date of Patent: May 17, 2022

(54) PERCUTANEOUS HEART PUMP TRANSITIONABLE BETWEEN SEPARATED AND OPERATIONAL CONFIGURATIONS

(71) Applicant: TC1 LLC, St. Paul, MN (US)

(72) Inventors: Alexander King, Maple Grove, MN (US); David Panus, Maple Grove, MN (US); Tracee Eidenschink, Wayzata, MN (US); John Pocrnich, Roseville, MN (US); Kevin Griffin, Elk River, MN (US)

(73) Assignee: TC1 LLC, St. Paul, MN (US)

( * ) Notice: Subject to any disclaimer, the term of this patent is extended or adjusted under 35 U.S.C. 154(b) by 0 days.

(21) Appl. No.: 16/390,366

(22) Filed: Apr. 22, 2019

(65) Prior Publication Data

US 2019/0321527 A1   Oct. 24, 2019

Related U.S. Application Data

(60) Provisional application No. 62/661,717, filed on Apr. 24, 2018.

(51) Int. Cl.
*A61M 60/148*   (2021.01)
*A61M 25/00*   (2006.01)
(Continued)

(52) U.S. Cl.
CPC ...... *A61M 60/205* (2021.01); *A61M 25/0023* (2013.01); *A61M 60/135* (2021.01);
(Continued)

(58) Field of Classification Search
CPC .... A61M 1/101; A61M 1/125; A61M 1/1008; A61M 1/1086; A61M 1/122;
(Continued)

(56) References Cited

U.S. PATENT DOCUMENTS

| | | | | |
|---|---|---|---|---|
| 4,753,221 A | * | 6/1988 | Kensey | A61M 60/205 600/16 |
| 7,011,620 B1 | * | 3/2006 | Siess | H02K 7/083 600/16 |

(Continued)

FOREIGN PATENT DOCUMENTS

WO   WO-2016028644 A1 *   2/2016 .......... A61M 60/857

OTHER PUBLICATIONS

International Search Report and Written Opinion for International Application No. PCT/US2019/028482, dated Jul. 25, 2019, 15 pages.
(Continued)

*Primary Examiner* — Carl H Layno
*Assistant Examiner* — Anh-Khoa N Dinh
(74) *Attorney, Agent, or Firm* — Armstrong Teasdale LLP

(57) ABSTRACT

Disclosed herein is a catheter pump that includes an expandable cannula and an impeller system. The expandable cannula defines a blood flow channel and includes an impeller blade zone, an inlet zone, and an outlet zone. The catheter pump further includes an impeller system including an impeller body, the impeller system movable relative to the expandable cannula along a longitudinal axis of the catheter pump. The catheter pump is selectively transitionable between a separated configuration in which the impeller
(Continued)

body is axially spaced from the expandable cannula along the longitudinal axis, and an operational configuration in which the impeller body is positioned within the impeller blade zone of the expandable cannula.

20 Claims, 8 Drawing Sheets

(51) Int. Cl.
    *A61M 25/04*     (2006.01)
    *A61M 60/205*     (2021.01)
    *A61M 60/135*     (2021.01)
    *A61M 60/50*     (2021.01)
    *A61M 60/857*     (2021.01)

(52) U.S. Cl.
    CPC ........... *A61M 25/04* (2013.01); *A61M 60/148* (2021.01); *A61M 60/50* (2021.01); *A61M 60/857* (2021.01); *A61M 2025/0024* (2013.01); *A61M 2025/0025* (2013.01)

(58) Field of Classification Search
    CPC ........... A61M 1/1024; A61M 25/0023; A61M 25/04; A61M 2025/0025; A61M 2025/0024; A61M 2025/0023
    See application file for complete search history.

(56) References Cited

U.S. PATENT DOCUMENTS

| | | |
|---|---|---|
| 8,597,170 B2 | 12/2013 | Walters et al. |
| 2011/0004046 A1* | 1/2011 | Campbell ........... A61M 60/135 600/16 |
| 2011/0311383 A1* | 12/2011 | White ................ F04D 29/0413 417/423.7 |
| 2012/0172655 A1* | 7/2012 | Campbell ............. A61M 25/04 600/16 |
| 2013/0303970 A1* | 11/2013 | Keenan ............... A61M 1/1024 604/9 |
| 2016/0319846 A1* | 11/2016 | Liebing ............... A61M 60/205 |
| 2017/0014562 A1* | 1/2017 | Liebing ................ F04D 29/181 |
| 2017/0087287 A1 | 3/2017 | Keenan et al. |
| 2018/0064862 A1 | 3/2018 | Keenan et al. |
| 2018/0243489 A1* | 8/2018 | Haddadi ............. A61M 60/205 |

OTHER PUBLICATIONS

Office Action issued in European Application No. 19732754.7, dated Oct. 20, 2021, 8 pages.

\* cited by examiner

PERCUTANEOUS HEART PUMP TRANSITIONABLE BETWEEN SEPARATED AND OPERATIONAL CONFIGURATIONS

CROSS REFERENCE TO RELATED APPLICATIONS

This application claims priority to provisional application Ser. No. 62/661,717, filed Apr. 24, 2018, which is incorporated herein in its entirety.

BACKGROUND OF THE DISCLOSURE a. Field of the Disclosure

The present disclosure relates generally to percutaneous heart pumps including an expandable cannula and an impeller body movable with respect to the expandable cannula along a longitudinal axis. More specifically, the present disclosure relates to a percutaneous heart pump, or a catheter pump, that has a separated configuration, wherein the impeller body and the expandable cannula are axially spaced from one another along a longitudinal axis of the catheter pump, and an operational configuration, wherein the impeller body is positioned at the same axial position as the expandable cannula.

b. Background

Heart disease is a major health problem that claims many lives per year. After a heart attack or other major cardiac event, only a small number of patients can be treated with medicines or other non-invasive treatment. A significant number of patients, however, can recover from a heart attack or other cardiac event if provided with mechanical circulatory support in timely manner.

In one conventional approach for treating patients, a blood pump having a fixed cross-section is surgically inserted a heart chamber, such as into the left ventricle of the heart and the aortic arch, to assist the pumping function of the heart. Other known conventional applications involve providing for pumping venous blood from the right ventricle to the pulmonary artery for support of the right side of the heart. The object of the surgically inserted pump is to reduce the load on the heart muscle for a period of time, which may be as long as a week, allowing the affected heart muscle to recover and heal. In some cases, surgical insertion may potentially cause additional stresses in heart failure patients.

In many cases, insertion of a left ventricular assist device (LVAD), a right ventricular assist device (RVAD), or in some cases a system for both sides of the heart (sometimes called biVAD) is a desirable alternative. The pump component of the device includes an impeller encased in a housing or expandable cannula, while blood, driven by the impeller, traverses the interior or lumen of the housing. Devices such as these, referred to as percutaneous heart pumps (PHPs), are often sheathed in a delivery device prior to being inserted percutaneously into the patient. The housing or expandable cannula is collapsible, or compressible, under a certain amount of force applied by the sheath. The force required to compress and sheath the housing or expandable cannula is increased when the impeller is located within the housing or expandable cannula, due to the size of the impeller.

It is desirable to reduce the sheathing force of PHPs to reduce the risk of damaging the housing or expandable cannula and the impeller. It is further recognized that the smaller the delivery profile of the sheathed catheter, the more readily it may be introduced into the patient's vasculature. However, it is also recognized that a larger operational profile enables increased blood flow at a lower impeller rotational velocity. Accordingly, a PHP maintaining a sufficiently small delivery profile and a sufficiently large operational profile, while reducing the necessary sheathing force is desired.

SUMMARY OF THE DISCLOSURE

The present disclosure is directed to a catheter pump including an expandable cannula defining a blood flow channel and including an impeller blade zone, an inlet zone, and an outlet zone. The catheter pump further includes an impeller system including an impeller body, the impeller system movable relative to the expandable cannula along a longitudinal axis of the catheter pump. The catheter pump is selectively transitionable between a separated configuration in which the impeller body is axially spaced from the expandable cannula along the longitudinal axis, and an operational configuration in which the impeller body is positioned within the impeller blade zone of the expandable cannula.

The present disclosure is further directed to a method of delivering a catheter pump having an expandable cannula and an impeller system to a target site. The method includes placing the catheter pump in a separated configuration, in which an impeller body of the impeller system is axially spaced from the expandable cannula along a longitudinal axis of the catheter pump, maneuvering the expandable cannula and impeller system to the target site while the catheter pump is in the separated configuration, and transitioning the catheter pump from the separated configuration to an operational configuration at the target site, wherein, in the operational configuration, the impeller body is located at the same axial position as the expandable cannula.

DETAILED DESCRIPTION OF THE DISCLOSURE

Figure 1:
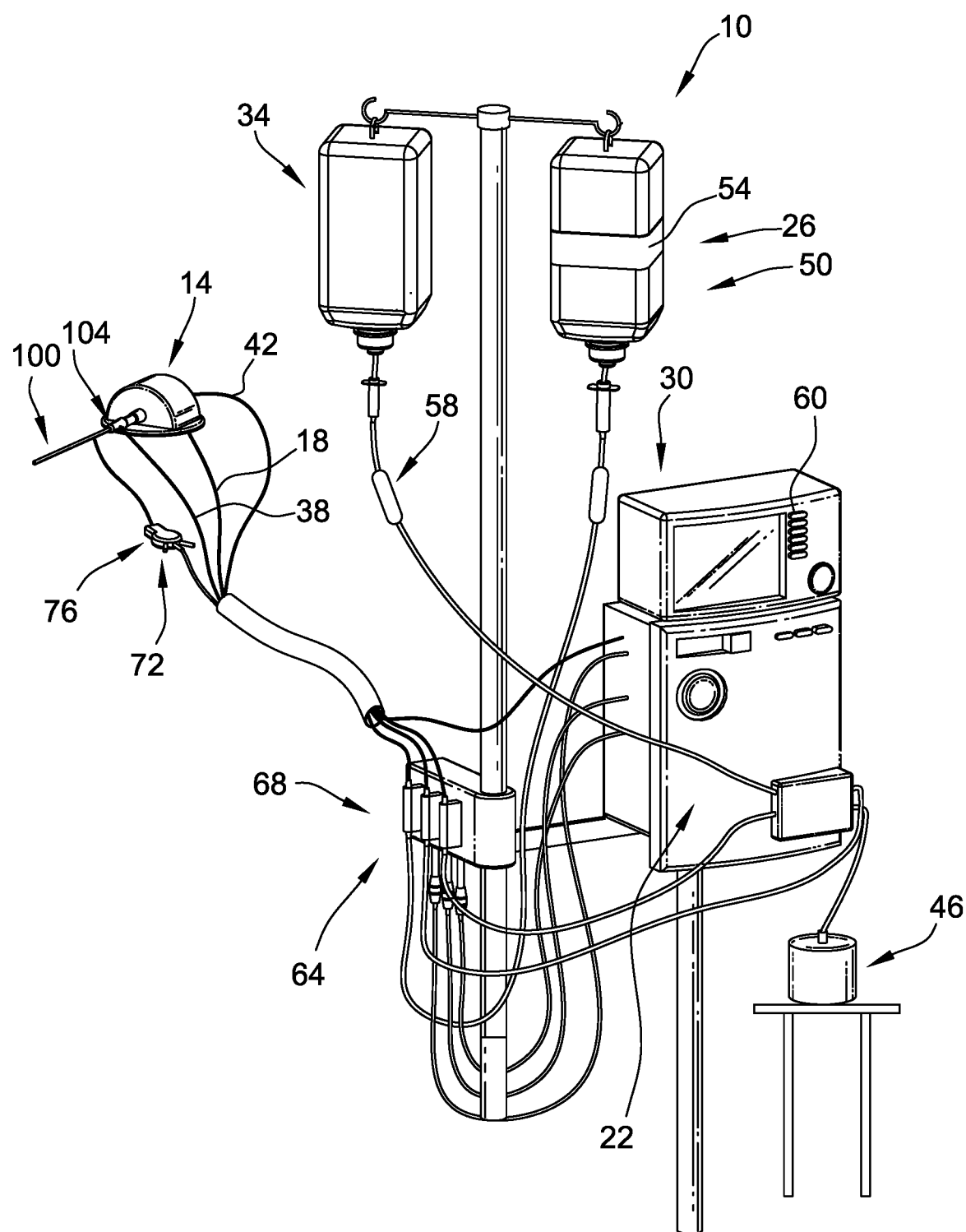
FIG. 1 illustrates one embodiment of a heart pump system configured for percutaneous application and operation.

Percutaneous heart pumps (PHP), also referred to as catheter pumps, and components of the present disclosure can be used to treat individuals experiencing cardiac stress, including acute heart failure. In particular, the catheter pumps of the present disclosure are configured such that the expandable housing, or expandable cannula, of the catheter pump and the impeller body are axially movable relative to one another along a longitudinal axis. Consequently, i.e., the expandable cannula and impeller body can be axially separated from one another in a separated configuration during delivery and/or removal, significantly reducing the force required to collapse components of the catheter pump.

Separating the impeller body and the expandable cannula reduces the cross-sectional delivery profile of the PHP as compared to a more conventional configuration where the impeller body is located within the expandable cannula during delivery. In embodiments of the PHP described herein, the impeller body moves longitudinally relative to the expandable cannula to enable each component to be collapsed, or compressed, individually (e.g., using a sheath or other delivery device), thereby achieving a reduced delivery profile while in the separated configuration. The reduced delivery profile eases percutaneous insertion of the PHP into the patient, and further enables the PHP to utilize a larger profile when the expandable cannula and impeller body expand to assume their operational shape and size. The impeller body is then moved longitudinally, and relative to the expandable cannula, in the proximal direction into an impeller blade zone of the expandable cannula. This defines the operational configuration.

An actuating mechanism for switching between the separated and operational configurations is located in the handle of the catheter. The impeller body moves longitudinally and proximally until a mechanical stop, e.g., a proximal bearing, positions it correctly in the impeller blade zone of the expandable cannula. In some embodiments, a follower magnet is included in the actuator mechanism. The follower magnet couples a motor to the impeller body only when the impeller system is properly positioned within the expandable cannula. This safety feature decreases opportunity for error and misuse of the PHP.

Additionally, axial separation of the impeller body and the expandable cannula renders a full-length hypotube unnecessary. Such a hypotube, or guidewire guide, enables tracking of a guidewire during insertion of the PHP through the patient's circuitous vasculature. However, with such PHPs, the guidewire and guidewire guide are removed after insertion of the PHP and, notably, the guidewire cannot be reinserted into the patient and the PHP cannot be repositioned without complete removal of the PHP from the patient. If the PHP is reusable, which is typically not the case, then the guidewire is reinserted into the catheter assembly and the PHP may be reinserted into the patient. More likely, the PHP is not reusable and must be discarded. Consequently, a new PHP and guidewire are needed. In either case, repeated introductions of the PHP may increase the duration of the procedure. In embodiments of the staggered PHP described herein, the guidewire may be reinserted without removing the PHP from the patient, which enables repositioning the PHP if necessary without the drawbacks associated with reintroducing the same or a new PHP and guidewire.

a. Catheter Pump System Overview

Figure 2:
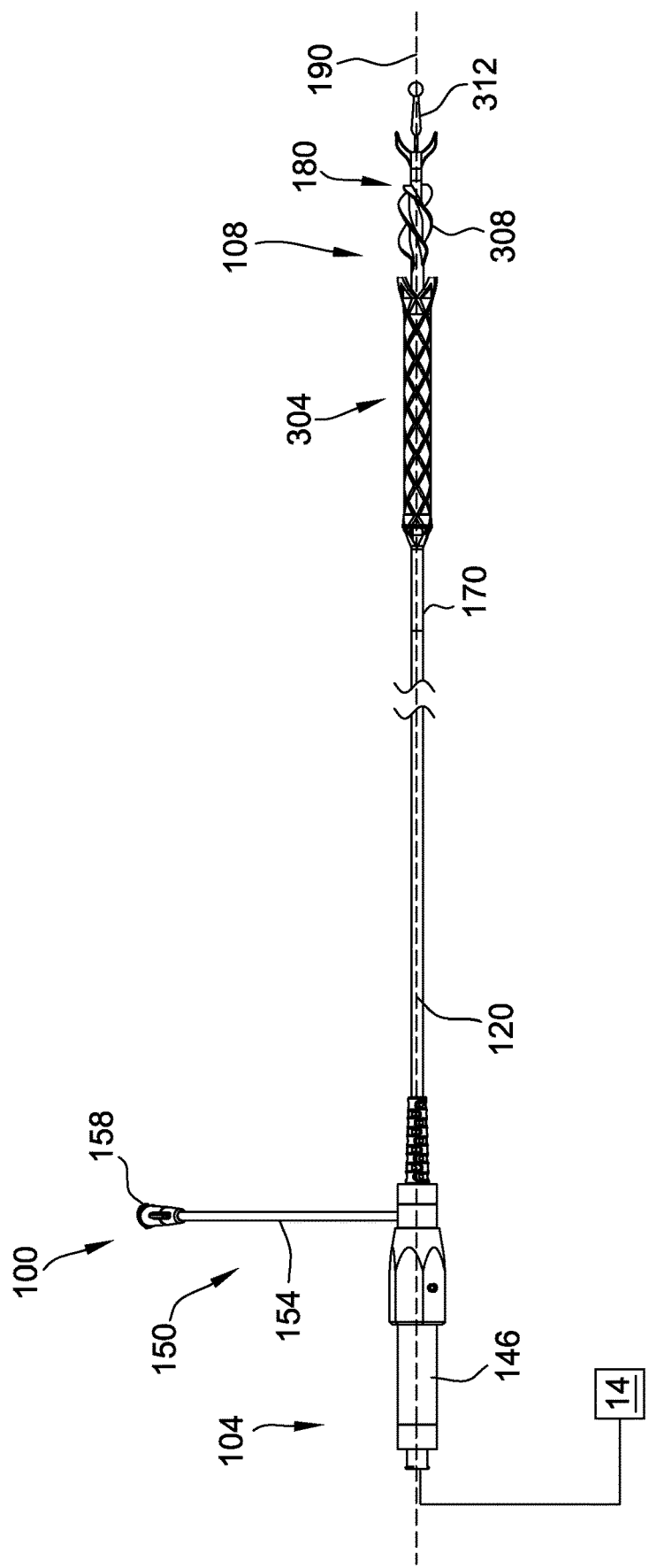
FIG. 2 illustrates one embodiment of a catheter assembly adapted to be used with the heart pump assembly of FIG. 1.

Referring now to the Figures, and specifically to FIG. 1 and FIG. 2, there is illustrated one embodiment of a heart pump 10 (note that heart pump and catheter pump are used interchangeably herein) that includes a catheter assembly 100 having a proximal end 104 adapted to connect to a motor 14 and a distal end 108 (shown in FIG. 2) adapted to be inserted percutaneously into a patient (not shown). Motor 14 is connected by a signal line 18 to a control module 22 that provides power and/or control signals to motor 14. Heart pump 10 may have an infusion system 26 and a patient monitoring system 30.

Infusion system 26 can provide a number of benefits to heart pump 10. In one embodiment, infusion system 26 includes an infusant source 34, a fluid conduit 38 extending from infusant source 34 to proximal end 104 of catheter assembly 100, and a fluid conduit 42 extending from proximal end 104 of catheter assembly 100 to a waste container 46. The flow of an infusant to and from catheter assembly 100 can be by any means, including a gravity system or one or more pumps. In FIG. 1, infusant source 34 includes an elevated container 50, which may contain saline or another infusant as necessary based on patient requirements. Flow from elevated container 50 can be regulated by a pressure cuff 54 (e.g., to elevate the pressure of the fluid in container 50 to increase flow), by a pinch valve 58, and/or by other suitable means.

With further reference to FIG. 1, patient monitoring system 30 enables monitoring the operation of the patient and/or pump 10. For example, patient monitoring system 30 can include a user interface 60 coupled with data source 64. Data source 64 can include one or more patient condition sensors, such as pressure sensors 68 that are in pressure communication with the patient and/or operating components within the patient. In one embodiment, pressure sensors 68 fluidly communicate by a conduit 72 that extends between the sensors and a proximal portion of catheter assembly 100. Conduit 72 can include a plurality of separable segments and can include a valve 76 to enable or disable the pressure communication to sensors 68.

Heart pump 10 is adapted to provide an acute or other short-term treatment. A short-term treatment can be for less than a day or up to several days or weeks in some cases. With certain configurations pump 10 can be used for a month or more.

FIG. 2 illustrates one embodiment of catheter assembly 100 that may be used with heart pump 10 (shown in FIG. 1). An impeller system 180 (described in detail herein) disposed at distal end 108 is configured to pump blood proximally or distally through or along a portion of heart pump 10 to convey blood from one body cavity to another. Impeller system 180 includes an impeller body 308. Impeller system 180 can be arranged to pump blood distally, such as in a right heart assist mode to move blood from the right ventricle to the pulmonary artery. On contrast, proximal flow is optimal for left heart support to move blood from the left ventricle to the aorta. Heart pump 10 can be used to treat patients with acute heart failure, ST elevation myocardial infarction (STEMI), cardiac arrest, cardiac arrhythmia or other heart conditions as noted above. Heart pump 10 also can be used in connection with a surgical treatment to support the patient without providing full cardiovascular bypass. A patient could be supported on the device for longer term with proper controls and design.

One feature that facilitates percutaneous insertion is configuring catheter assembly 100 to have a relatively low delivery profile. Accordingly, in the embodiments described herein, catheter assembly 100 is selectively switchable between a separated configuration, which may be used for delivery of catheter assembly 100 to a pumping site, and an operational configuration (i.e., for operation of catheter assembly 100 at the pumping site). As the separated configuration is used for delivery of catheter assembly 100, the separated configuration may also be referred to as a delivery configuration. In the separated configuration, impeller body 308 is axially spaced from an expandable cannula 304 along a longitudinal axis 190 of catheter assembly 100. In FIG. 2, catheter assembly 100 is shown in the separated configuration. On the other hand, in the operational configuration, impeller body 308 is located at the same axial position as expandable cannula 304. Specifically, impeller body 308 is positioned within expandable cannula 304. The separated and operational configurations are described in detail herein.

Catheter assembly 100 is capable of being compressed or otherwise reduced to a substantially smaller cross-sectional profile in the separated configuration, relative to the operational configuration. For example, distal end 108 of catheter assembly 100 may have a cross-sectional profile of approximately 11 French (approximately 3.5 mm) in the separated configuration and a cross-sectional profile of approximately up to about 21 French (approximately 7 mm) in an operational configuration. The larger profile in the operational configuration facilitates greater blood flow rates driven by impeller system 180. Although the above examples have been given, those of skill in the art will appreciate that other sizes for the separated and operational configurations are within the scope of the present disclosure.

Catheter assembly 100 is configured to position distal end 108 in a heart chamber after being inserted initially into a peripheral vessel. For example, catheter assembly 100 may have a suitable length to reach the left ventricle and sufficient maneuverability and torquability to traverse the intervening vasculature. In this embodiment, catheter assembly 100 includes a multilumen catheter body 120 that is arranged to facilitate delivery and operation of impeller system 180 and expandable cannula 304. Further details concerning various embodiments of the catheter body 120 are described in more detail in U.S. Pat. No. 8,597,170, filed Jan. 34, 2012, which is incorporated by reference herein in its entirety.

A drive system drives (i.e., rotates) one or more components of impeller system 180, such as impeller body 308. The drive system includes motor 14 coupled to a drive controller (not shown). The drive controller may be integrated into control module 22 (shown in FIG. 1). Although motor 14 may be configured to be disposed outside of the patient, in some embodiments, motor 14 may be sufficiently small such that motor is insertable into the patient during use, including into the vasculature.

A torque coupling system transfers torque from motor 14 to impeller system 180. An example torque coupling system is discussed further in U.S. Pat. No. 8,597,170, but in general may include a mechanical or magnetic interface disposed between motor 14 and a drive assembly disposed at proximal end 104 of catheter assembly 100. The drive assembly is coupled with a proximal end of an elongate drive shaft (not shown in FIG. 2) that extends through catheter body 120. A distal portion of the drive shaft is coupled to impeller system 180.

In at least some embodiments, motor 14 does not engage impeller system 180 unless impeller body 308 is properly positioned within expandable cannula 304. Accordingly, impeller body 308 cannot be driven by motor 14 when catheter assembly 100 is in the separated configuration.

FIG. 2 further shows an infusion inflow assembly 150 that can form a part of infusion system 26 (see FIG. 1). Infusion inflow assembly 150 is provided adjacent proximal end 104 in one embodiment. Infusion system 26 is configured to convey one or more fluids through catheter assembly 100 during operation of impeller system 180. In one embodiment, an infusant, e.g., a medication or a lubricating fluid, such as saline or other beneficial medium, is conveyed distally along the pump, e.g., within catheter body 120, toward the operating components adjacent to distal end 108. The infusant can include lubrication fluids such as glucose or other biocompatible lubricants. Infusion inflow assembly 150 includes an infusion body 154 having a luer or other suitable connector 158 disposed at a proximal end thereof and in fluid communication with one or more lumens within catheter assembly 100. A lumen extending through infusion body 154 is adapted to be fluidly coupled with a fluid source connected to connector 158, to deliver the fluid into catheter assembly 100. In some embodiments, catheter assembly 100 further includes an outer sheath (omitted in FIG. 2 for clarity) capable of selectively covering at least one of impeller system 180 and expandable cannula 304.

As shown in FIG. 2, distal end 108 of catheter assembly 100 includes an atraumatic tip 312 disposed distal of impeller body 308. Atraumatic tip 312 generally has an arcuate configuration such that atraumatic tip 312 does not injure tissue when contacting tissue (e.g., the inner wall or endocardial surface of the ventricle). In some embodiments, atraumatic tip 312 may include a 180° bend (not shown in the Figures), such that atraumatic tip 312 forms a J-shaped tip. In yet another embodiment, the distal-most end of atraumatic tip 312 may include one or more coils, forming a pigtail-shaped tip.

Figure 3:
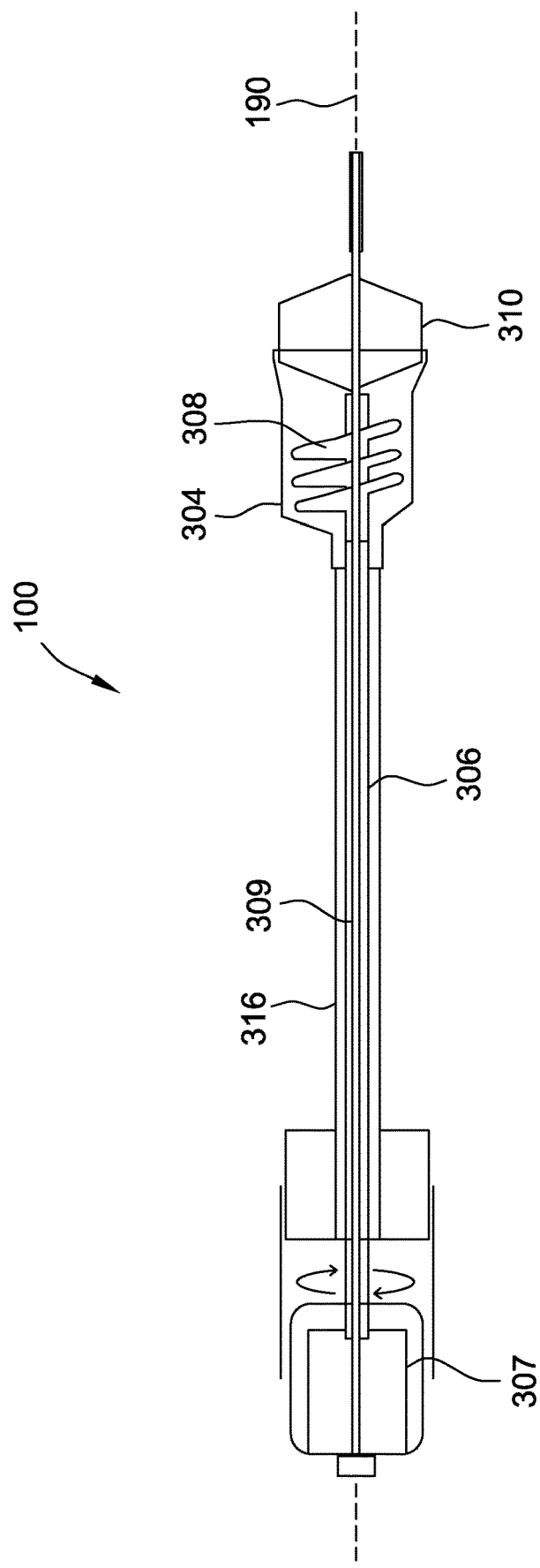
FIG. 3 illustrates a schematic view of the catheter assembly shown in FIG. 2.

FIG. 3 is a schematic view of catheter assembly 100, showing various components of catheter assembly 100. Further, FIG. 3 shows catheter assembly 100 in the operational configuration. That is, FIG. 3 shows impeller body 308 located at the same axial position (relative to longitudinal axis 190) as expandable cannula 304 and positioned within expandable cannula 304.

Impeller body 308 is coupled to an impeller shaft 306, also referred to as a torque cable. Further, impeller shaft 306 is coupled to a motor shaft 307 driven by motor 14 (shown in FIG. 2). Accordingly, when motor 14 rotates motor shaft 307, impeller shaft 306 and impeller body 308 also rotate.

A guidewire lumen 309 extends through motor shaft 307, impeller shaft 306, and impeller body 308. That is, motor shaft 307, impeller shaft 306, and impeller body 308 define a passageway that receives guidewire lumen 309. Further, guidewire lumen 309 defines a passageway sized to receive a guidewire (e.g., during delivery of catheter assembly 100) therethrough.

As shown in FIG. 3, guidewire lumen 309 extends distally beyond impeller body 308. Further, guidewire lumen 309 is coupled to a distal bearing 310 located distal of impeller body 308. Guidewire lumen 309 continues to extend distally beyond distal bearing 310, and terminates in or couples to atraumatic tip 312 (not shown in FIG. 3). In some embodiments, catheter assembly 100 does not include distal bearing 310.

In this embodiment, there is a radial clearance between guidewire lumen 309 and motor shaft 307, impeller shaft 306, and impeller body 308. This clearance allows motor shaft 307, impeller shaft 306, and impeller body 308 to all rotate about guidewire lumen 309 during operation of impeller system 180. That is, guidewire lumen 309 (as well as distal bearing 310 and atraumatic tip 312) are substantially stationary during rotation of impeller body 308.

Expandable cannula 304 is also stationary during rotation of impeller body 308. Further, as shown in FIG. 3, expandable cannula 304 is coupled to a cannula shaft 316, which is also stationary during rotation of impeller body 308. Cannula shaft 316 is substantially hollow, and impeller shaft 306 and guidewire lumen 309 extend through cannula shaft 316.

Figure 4A:
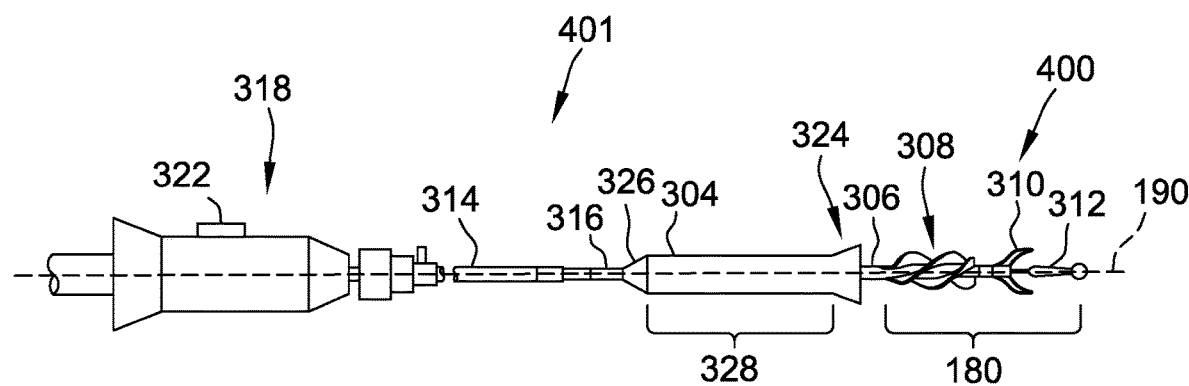
FIG. 4A illustrates one embodiment of a catheter assembly in a separated configuration.
Figure 4B:
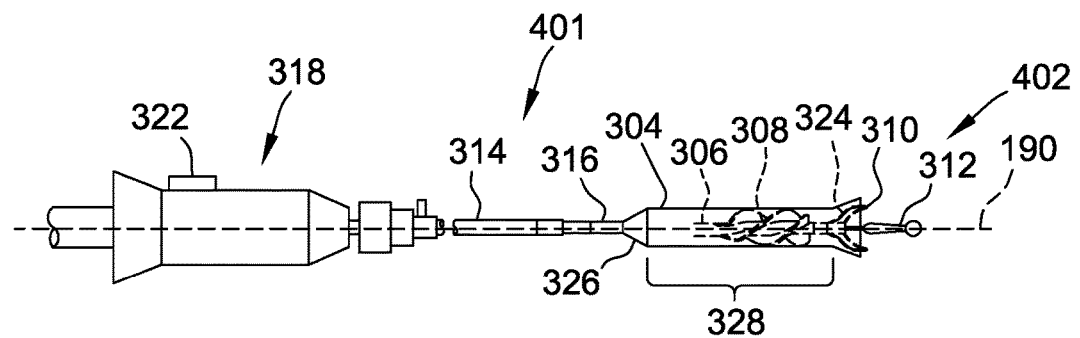
FIG. 4B illustrates the catheter assembly of FIG. 4A in an operational configuration.
Figure 5A:
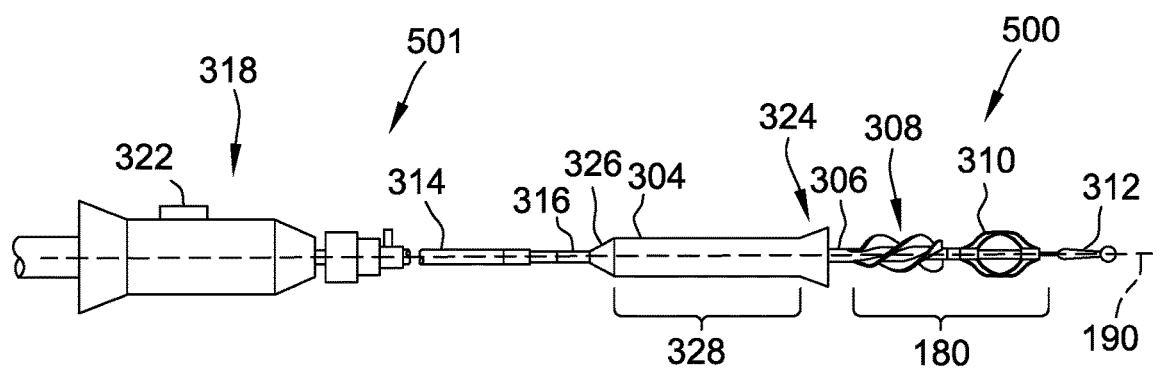
FIG. 5A illustrates another embodiment of a catheter assembly in a separated configuration.
Figure 5B:
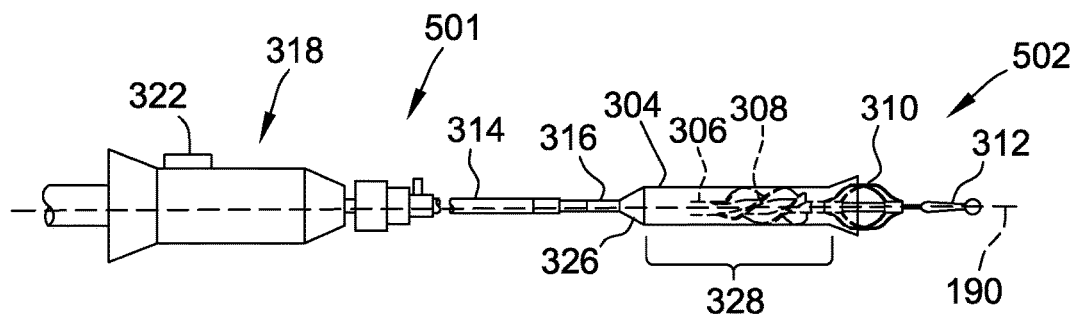
FIG. 5B illustrates the catheter assembly of FIG. 5A in an operational configuration.

FIGS. 4A and 4B illustrate a separated configuration 400 and an operational configuration 402 of one embodiment of a catheter assembly 401. FIGS. 5A and 5B illustrate a separated configuration 500 and an operational configuration 502 of another embodiment of a catheter assembly 501. Unless otherwise indicated, components of the catheter assemblies 401 and 501 are substantially similar to those of catheter assembly 100.

In separated configurations 400 and 500, expandable cannula 304 and impeller body 308 are axially spaced from one another along longitudinal axis 190. This allows expandable cannula 304 and impeller body 308 to be compressed or collapsed (e.g., using a sheath or other delivery device) separate from one another, which results in an overall smaller cross-sectional delivery profile of expandable cannula 304 and impeller body 308.

In contrast, in operational configurations 402 and 502, expandable cannula 304 and impeller body 308 are located at the same axial position along longitudinal axis 190, such that impeller body 308 is positioned within expandable cannula 304. Expandable cannula 304 defines an inlet zone 324, an outlet zone 326, and an impeller blade zone 328 between inlet zone 324 and outlet zone 326. In at least some embodiments, inlet zone 324 is has a larger cross-sectional area than outlet zone 326 of expandable cannula 304. In operational configurations 402 and 502, impeller body 308 is positioned within impeller blade zone 328 of expandable cannula 304. Further, as described above, impeller system 180 includes impeller shaft 306, impeller body 308 coupled to impeller shaft 306, distal bearing 310, and atraumatic tip 312.

In some embodiments, a distal end of expandable cannula 304 flares radially outward relative to longitudinal axis 190. As shown in FIGS. 4B and 5B, in operational configurations 402 and 502, distal bearing 310 engages the flared distal end of expandable cannula 304, securing impeller system 180 relative to expandable cannula 304. This is also shown in FIG. 3.

In catheter assembly 401, distal bearing 310 is a partial basket, or half-basket bearing. In contrast, in catheter assembly 501, distal bearing 310 is a full basket bearing. Partial basket bearings may be beneficial in reducing overall delivery length of a catheter assembly. On the other hand, full basket bearings, while more complex, may provide a stronger and more uniform radial force to interface with expandable cannula 304, and may have improved integration with atraumatic tip 312.

In the exemplary embodiment, an outer sheath 314 is configured to selectively cover expandable cannula 304 and impeller system 180. In FIGS. 4A, 4B, 5A, and 5B, for clarity, outer sheath 314 is shown in an unsheathed position (i.e., not covering expandable cannula 304 and impeller system 180). However, during delivery, outer sheath 314 generally covers expandable cannula 304 and impeller system 180, at least partially collapsing expandable cannula 304 and impeller system 180 into a delivery profile, and further reducing the cross-sectional profile of expandable cannula 304 and impeller system 180.

To transition between the separated configuration and the operational configuration, catheter assemblies 401 and 501 include an actuator 318. For example, actuator 318 may be implemented as first and second components that are slidable relative to one another, the first component coupled to impeller system 180 and the second component coupled to expandable cannula 304. One such embodiment is described below in association with FIGS. 6A and 6B.

Further, in some embodiments, an input device 322 on actuator 318 allows a user to selectively transition catheter assemblies 401 and 501 between the separated configuration and the operational configuration. Input device 322 may be a knob or a button. For example, a knob coupled to a first component (which is in turn coupled to impeller system 180) may assist a user in sliding the first component relative to a second component coupled to expandable cannula 304. One such embodiment is described below in association with FIGS. 7A and 7B. Alternatively, input device 322 may be any device that enables a user to transition catheter assemblies 401 and 501 between the separated configuration and the operational configuration.

Further, in other embodiments, actuator 318 may include other suitable components for selectively transitioning catheter assembly 401 and 501 between the separated configuration and the operational configuration. For example, in some embodiments, actuator includes a spring (not shown) or other biasing mechanism that biases actuator towards one of the separated configuration and the operational configuration. In such an embodiment, activating the input device 322 (e.g., pressing a button) allows the spring to expand, causing a transition from one configuration to the other. In other embodiments, an actuator motor (not shown) or other electromechanical device may be used to selectively transition catheter assembly 401 and 501 between the separated configuration and the operational configuration. In such embodiments, operation of the actuator motor (e.g., in response to a user depressing a button) causes impeller system 180 to translate relative to expandable cannula 304.

In addition, in some embodiments, actuator 318 includes one or more visual indicators that enable a user to quickly and easily ascertain whether the catheter assembly 401 or 501 is in the separated configuration or the operational configuration. The visual indicators may include, for example, one or more indicia on actuator 318 that are only visible when catheter assembly 401 or 501 is in one of the separated configuration or the operational configuration (and not visible in the other configuration), a gauge or other readout indicating the current configuration, etc.

Further, in some embodiments, a locking mechanism (not shown) maintains catheter assembly 401 or 501 in the operational configuration. Accordingly, during operation, catheter assembly 401 or 501 cannot be inadvertently or accidentally transitioned from the operational configuration to the separated configuration. Instead, to transition from the operational configuration to the separated configuration, the user would have to first disengage the locking mechanism.

As described above, during delivery, catheter assembly 401 or 501 is in the separated configuration (shown in FIGS. 4A and 5B). Once a target site is reached, a user engages input device 322 (e.g., by depressing a button), causing actuator 318 to transition catheter assembly 401 or 501 from the separated configuration the operational configuration. Specifically, in response to user engaging input device 322, impeller body 308 translates proximally along longitudinal axis 190 relative to expandable cannula 304, and into impeller blade zone 328 of expandable cannula 304.

To transition catheter assembly 401 or 501 back to the separated configuration (e.g., to reposition or withdraw catheter assembly 401 or 501), the user again engages input device 322. Specifically, in response to user engaging input device 322, impeller body 308 translates distally along longitudinal axis 190 relative to expandable cannula 304, and out of impeller blade zone 328.

Figure 6A:
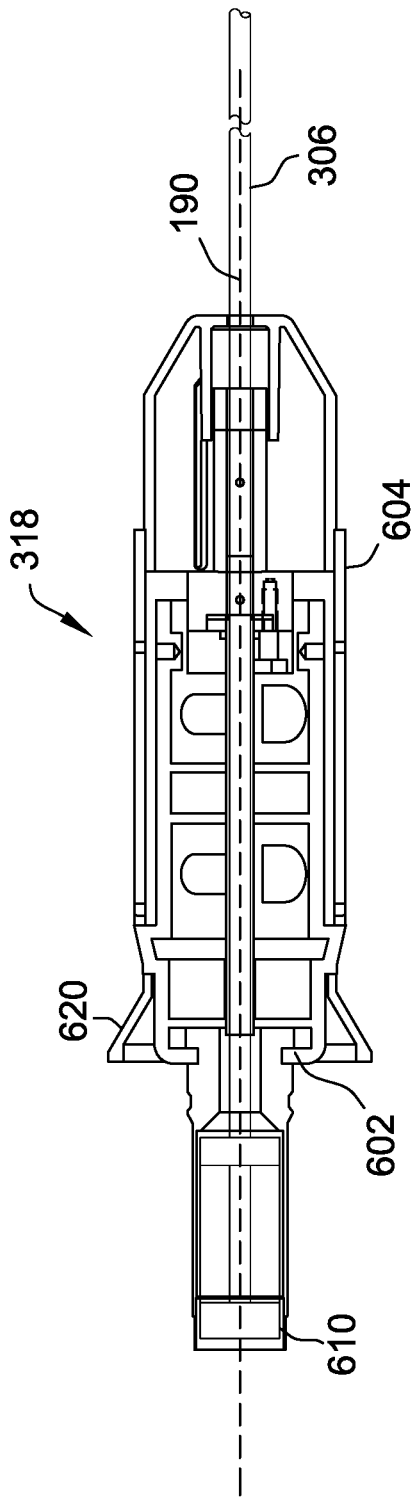
FIG. 6A illustrates an actuator for use with the catheter assemblies of FIGS. 3A, 3B, 4A, and 4B in a separated configuration.
Figure 6B:
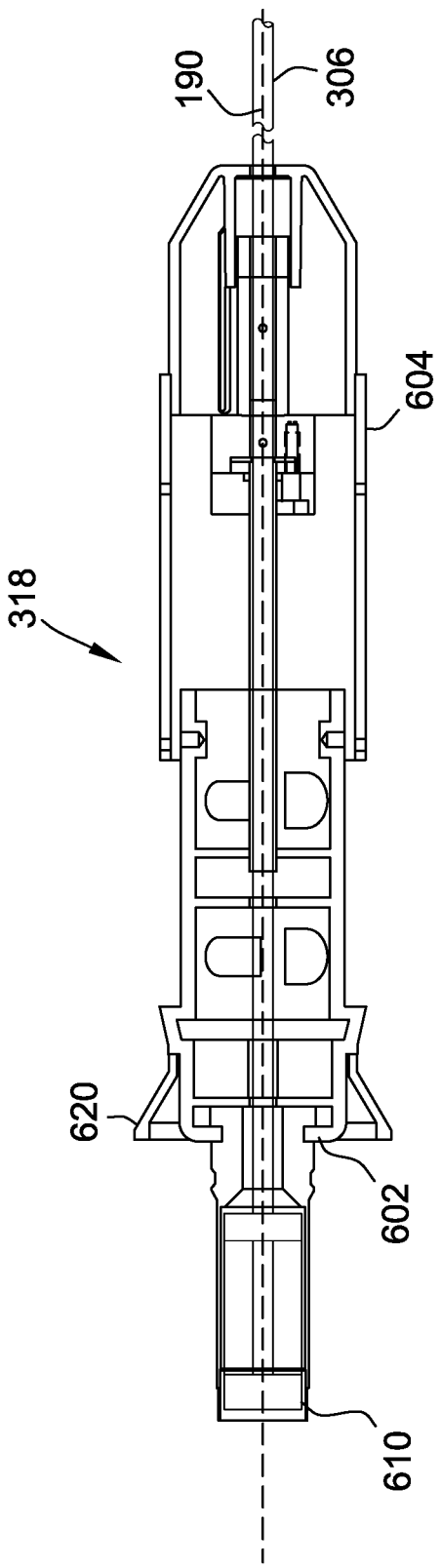
FIG. 6B illustrates the actuator of FIG. 6A in an operational configuration.

FIGS. 6A and 6B show on embodiment of actuator 318 in the separated configuration and the operational configuration, respectively. As shown in FIGS. 6A and 6B, in this embodiment, actuator 318 includes an impeller anchor 602 and a cannula anchor 604. Further, in FIGS. 6A and 6B, impeller shaft 306 is shown coupled to a follower magnet 610 of motor 14 that is operable to drive impeller shaft 306. Impeller anchor 602 is slidable (i.e., along longitudinal axis 190) relative to cannula anchor 604. Impeller anchor 602 is coupled to impeller shaft 306 such that translating impeller anchor 602 along longitudinal axis 190 causes impeller shaft 306 (and thus, impeller body 308) to translate along longitudinal axis 190. Further, although impeller shaft 306 translates with impeller anchor 602, impeller shaft 306 is also rotatably coupled to impeller anchor 602 (e.g., using rotary bearings (not shown)) such that impeller shaft 306 is rotatable relative to impeller anchor 602. Further, in this embodiment, cannula anchor 604 is fixedly coupled to expandable cannula 304 and cannula shaft 316.

Accordingly, sliding impeller anchor 602 relative to cannula anchor 604 causes impeller body 308 to translate relative to expandable cannula 304 along longitudinal axis 190. As explained above, FIG. 6A shows actuator 318 in the separated configuration and FIG. 6B shows actuator 318 in the operational configuration. Accordingly, when transitioning from the separated configuration to the operational configuration, impeller anchor 602 slides proximally relative to cannula anchor 604. This causes impeller body 308 to slide proximally relative to expandable cannula 304, and into impeller blade zone 328 of expandable cannula 304.

On the other hand, when transitioning from the operational configuration to the separated configuration, impeller anchor 602 slides distally relative to cannula anchor 604. This causes impeller body 308 to slide distally relative to expandable cannula 304, and out of impeller blade zone 328 of expandable cannula 304. In the embodiment shown in FIGS. 6A and 6B, a flared portion 620 of actuator 318 is part of impeller anchor 602 and moves with impeller anchor 602. Impeller anchor 602 may be slid relative to cannula anchor 604 using any input device 322.

Figure 7A:
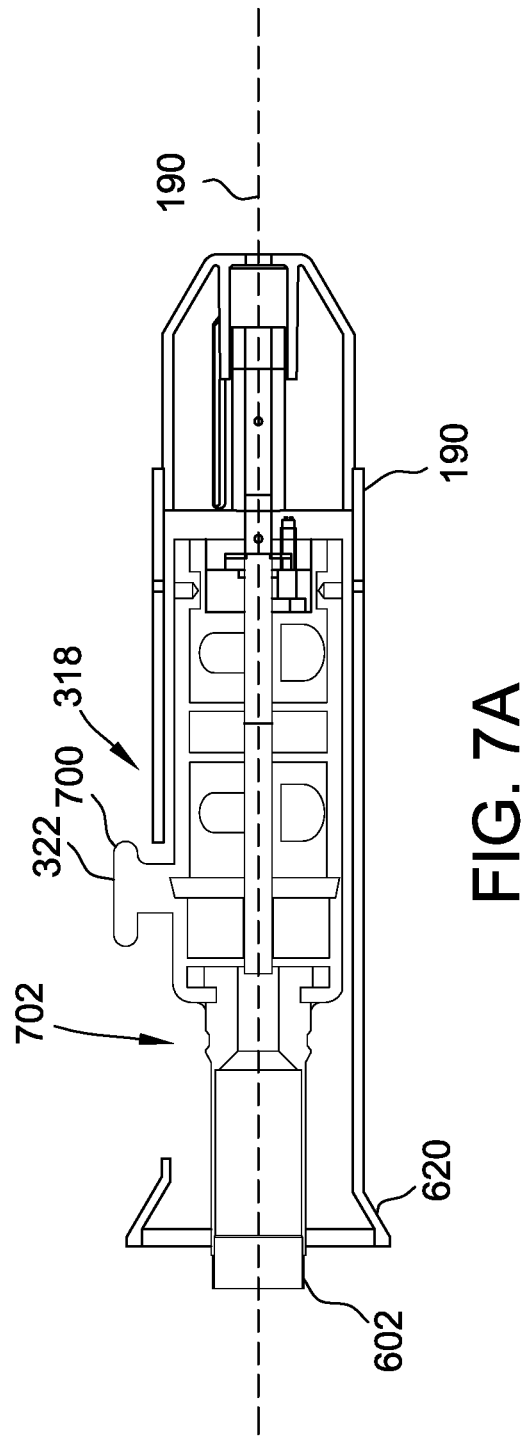
FIG. 7A illustrates another embodiment of an actuator for use with the catheter assemblies of FIGS. 3A, 3B, 4A, and 4B in a separated configuration.
Figure 7B:
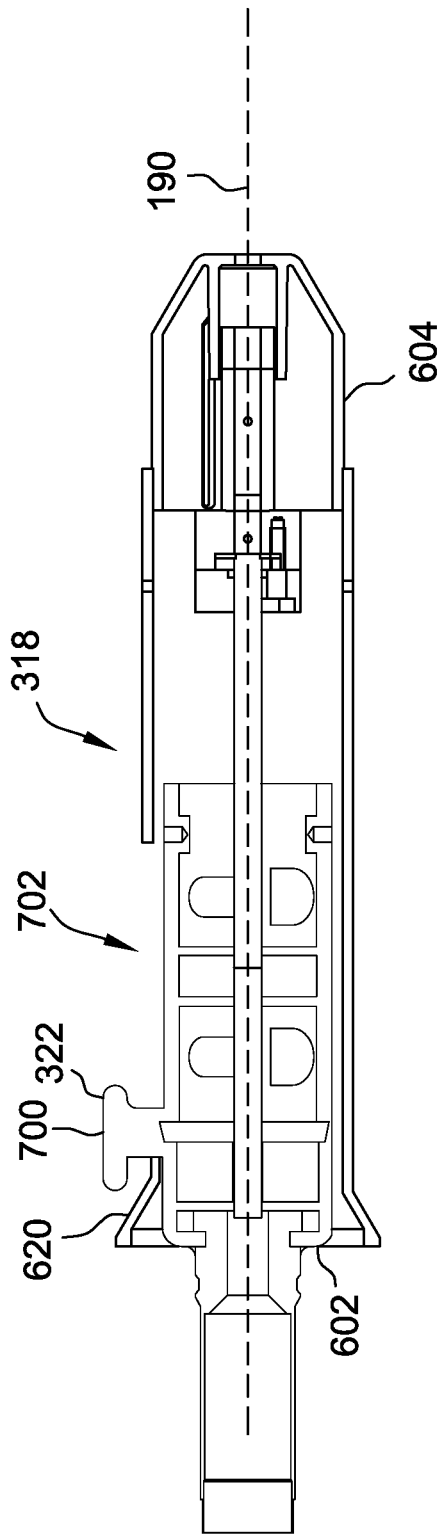
FIG. 7B illustrates the actuator of FIG. 7A in an operational configuration.

For example, FIGS. 7A and 7B depict an embodiment of actuator 318 in which input device 322 is a slidable knob 700 that is fixedly coupled to impeller anchor 602. Slidable knob 700 extends radially outward from impeller anchor 602 through a slot 702 defined in cannula anchor 604 and extending generally parallel to longitudinal axis 190. Further, slidable knob 700 is capable of translating along slot 702 (i.e., in a direction generally parallel to longitudinal axis 190). As slidable knob 700 translates along slot 702, impeller anchor 602 slides relative to cannula anchor 604, transitioning actuator 318 between the separated configuration and the operational configuration. In the embodiment shown in FIGS. 7A and 7B, flared portion 620 of actuator 318 is part of cannula anchor 604 and moves with cannula anchor 604.

In some embodiments, slidable knob 700 may be biased (e.g., using a spring) toward one of the separated configuration and the operational configuration. Further, in some embodiments, slot 702 may be partially defined by a seat or shoulder (e.g., a surface generally perpendicular to longitudinal axis 190) against which slidable knob 700 rests in the separated configuration and/or the operational configuration. Alternatively, input device 322 may be any device that enables transitioning between the separated configuration and the operational configuration.

In some embodiments, at least one component of catheter assembly 100 includes a memory shape material. For example, expandable cannula 304 may include a memory shape alloy. Memory shape alloys (sometimes referred to as shape memory alloys or materials) are compositions that can be deformed under stress but return to a specific shape once that stress is released. A substrate that includes a memory shape alloy will return to its original shape multiple times with the application and release of deforming stress. Further, the change in shape of the substrate will also affect any coating on the surface of the substrate, and as such, any coating applied to the memory shape alloy should also be able to change shape without undergoing degradation.

Memory shape alloys display two distinct crystal forms: martensite and austenite. The temperature and the internal stress of the system determines the crystal form of a material. The martensite form typically exists at lower temperature while the austenite form exists at higher temperatures. At low temperatures, the martensite can be readily deformed and shaped. When the temperature increases and the crystal form changes from martensite to austenite, the austenite form "remembers" the shape it had before it was deformed and reverts back to that shape. Repeated use of the shape-memory effect may lead to a shift of the characteristic transformation temperatures (called functional fatigue) because it is closely related to the change in microstructural and functional properties of the material.

Examples of memory shape alloys suitable for use herein include, but are not limited to, nickel-titanium (nitinol), copper-zinc, copper-zinc-aluminum, copper-aluminum-nickel, and gold-cadmium.

Because the surface of expandable cannula 304 is exposed to the vasculature of a patient, in some embodiments, expandable cannula 304 is covered with a flexible material. In some aspects, the flexible material is a biocompatible thermoplastic elastomer.

In some aspects, the biocompatible thermoplastic elastomer is independently selected from the group consisting of a poly(urethane) block copolymer having both hard blocks and soft blocks, a poly(ether amide) block copolymer, poly(ether ester) block copolymer, a poly(olefin) vulcanized to comprise polar functional groups, a poly(styrene) vulcanized to comprise polar functional groups and combinations thereof. In some embodiments, the biocompatible thermoplastic elastomer comprises a poly(olefin) vulcanized to comprise polar functional groups and/or a poly(styrene) vulcanized to comprise polar functional groups where the functional groups are selected from the group consisting of maleic anhydride, acrylate, epoxy, amine, and combinations thereof.

In some aspects, the polymer is a poly(urethane) block copolymer comprising at least one additional polymer block where, in addition to the poly(urethane) block, the at least one additional block is selected from the group consisting of poly(ether), poly(carbonate), poly(silane), poly(siloxane), poly(styrene), poly(vinylalcohol), poly(meth)acrylate, poly(acrylate), poly(urea), poly(urethane), poly(ethylene), poly(tetrafluoroethylene), poly(phenol), poly(ester), poly(amide), poly(peptide), and combinations thereof. If a second poly(urethane) is used, then the specific monomers used to prepare each poly(urethane) will be different, or the properties of each block will be different from one another.

Specific examples include, but are not limited to, Thoralon®, Carbosil®, Pursil®, Pellethane®, Elast-Elon®, Pellethane®, Tecoflex®, Tecothane®, Bionate®, Elast-Eon®, Pebax®, Vestamid®, Hytrel®, Arnitel®, Santoprene®, Selas®, Zelas®, Tresprene®, Kraton® and combinations thereof. Desirably, the biocompatible thermoplastic elastomer is Thoralon®.

In yet another aspect, the biocompatible thermoplastic elastomer is a poly(urethane) block copolymer. When the polymer has two or more blocks, each block may be the same or different than any other block. For example, two different poly(urethanes) may be combined in a block copolymer. In another example, a poly(urethane-urea) block polymer is used. In yet another example, a poly(ether-siloxane-urethane) block polymer is used.

Figure 8:
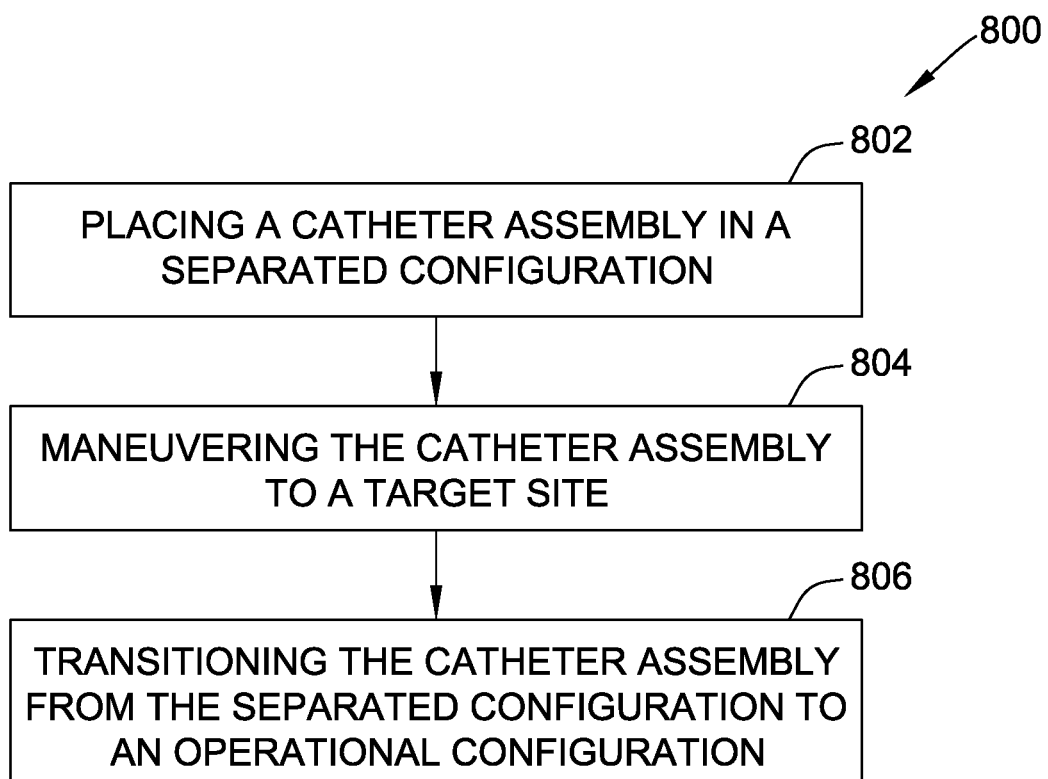
FIG. 8 is a flow diagram illustrating one embodiment of a method for delivering a catheter assembly to a target site.

Also disclosed herein is method 800 for delivering or inserting catheter assembly having an expandable catheter and an impeller body to a target site. With reference to FIG. 8, method 800 includes placing 802 the catheter assembly in a separated configuration. In the separated configuration, an impeller body is axially spaced from the expandable catheter along a longitudinal axis of the catheter assembly. Method 800 further includes maneuvering 804 the catheter assembly to the target site while the catheter assembly is in the separated configuration. Method 800 further includes transitioning 806 the catheter assembly from the separated configuration to an operational configuration at the target site. In the operational configuration, the impeller body is at the same axial position as the expandable cannula, and the impeller body is positioned inside of the expandable cannula. In some embodiments, transitioning 806 the catheter assembly includes moving a slidable knob on an actuator.

Although the embodiments and examples disclosed herein have been described with reference to particular embodiments, it is to be understood that these embodiments and examples are merely illustrative of the principles and applications of the present disclosure. It is therefore to be understood that numerous modifications can be made to the illustrative embodiments and examples and that other arrangements can be devised without departing from the spirit and scope of the present disclosure as defined by the claims. Thus, it is intended that the present application cover the modifications and variations of these embodiments and their equivalents.

This written description uses examples to disclose the disclosure, including the best mode, and also to enable any person skilled in the art to practice the disclosure, including making and using any devices or systems and performing any incorporated methods. The patentable scope of the disclosure is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. A catheter pump, comprising:
    an expandable cannula defining a blood flow channel and comprising an impeller blade zone, a single inlet zone including a flared portion that widens radially between a proximal end and a distal end to receive and securely engage a bearing assembly, and an outlet zone; and
    an impeller system comprising an impeller body rotatably coupled to the bearing assembly, the impeller system movable relative to the expandable cannula along a longitudinal axis of the catheter pump,
    wherein the catheter pump is selectively transitionable between a separated configuration in which the impeller body and the bearing assembly are axially spaced from the expandable cannula along the longitudinal axis, and an operational configuration in which the impeller body is positioned within the impeller blade zone of the expandable cannula and the bearing assembly is engaged with the flared portion, thereby securing the impeller system relative to the expandable cannula, and
    wherein when the catheter pump is in the separated configuration, the inlet zone includes the flared portion, such that the flared portion is not held open by the bearing assembly and such that the flared portion is sizeable and shapeable according to a size and a shape of the impeller body and the bearing assembly before the impeller body and the bearing assembly are received.

2. The catheter pump of claim 1, wherein the impeller system further comprises a guidewire lumen extending through the impeller body.

3. The catheter pump of claim 2, wherein the impeller system further comprises an atraumatic tip coupled to the guidewire lumen.

4. The catheter pump of claim 1, wherein the expandable cannula comprises a tubular stent frame formed from a shape memory material selected from the group consisting of nickel-titanium, copper-zinc, copper-zinc-aluminum, copper-aluminum-nickel, gold-cadmium and combinations thereof.

5. The catheter pump of claim 1, wherein the expandable cannula is coated with a flexible material.

6. The catheter pump of claim 1, wherein the inlet zone of the expandable cannula has a larger cross-sectional area than the impeller blade zone of the expandable cannula.

7. The catheter pump of claim 6, wherein the bearing assembly is a partial basket bearing or full basket bearing.

8. The catheter pump of claim 7, wherein the impeller system is configured such that the bearing assembly remains substantially stationary with respect to the expandable cannula during rotation of the impeller body.

9. The catheter pump of claim 1, further comprising:
    an actuator configured to transition the catheter pump between the separated configuration and the operational configuration, the actuator including at least one indicium configured to visually indicate, outside a blood lumen of a patient when the impeller system is disposed within the blood lumen of the patient, at least one of i) that the catheter pump is in the separated configuration, or ii) that the catheter pump is in the operational configuration.

10. The catheter pump of claim 9, wherein the actuator comprises:
    an impeller anchor rotatably coupled to the impeller system near a proximal end thereof, whereby at least an impeller shaft of the impeller system is rotatable relative to the impeller anchor, and
    a cannula anchor coupled to the expandable cannula near a proximal end thereof, the impeller anchor slidable relative to the cannula anchor, whereby the impeller anchor is configured to translate axially relative to the cannula anchor to cause the catheter pump to transition between the separated configuration and the operational configuration.

11. The catheter pump of claim 10, wherein the impeller anchor is slidable relative to the cannula anchor by operation of a manually operable slidable knob fixedly coupled to the impeller anchor near a proximal end of the impeller system and extending radially outward from the impeller anchor through an opening defined by the cannula anchor.

12. A method of delivering a catheter pump having an expandable cannula and an impeller system to a target site, the method comprising:
    placing the catheter pump in a separated configuration, in which an impeller body of the impeller system is axially spaced from the expandable cannula along a longitudinal axis of the catheter pump;
    maneuvering the expandable cannula and impeller system to the target site while the catheter pump is in the separated configuration; and
    transitioning the catheter pump from the separated configuration to an operational configuration at the target site,
    wherein, in the operational configuration, the impeller body is located at the same axial position as the expandable cannula,
    wherein in the operational configuration, a bearing assembly, rotatably coupled to the impeller body, is at least partially received within a flared portion of a single inlet zone of the expandable cannula, such that the bearing assembly is held stationary via engagement with the flared portion, and
    wherein, when the catheter pump is in the separated configuration, the inlet zone includes the flared portion, such that the flared portion is not held open by the bearing assembly and such that the flared portion is sizeable and shapeable according to a size and a shape of the impeller body and the bearing assembly before the impeller body and the bearing assembly are received.

13. The method of claim 12, further comprising:
    inserting the expandable cannula and impeller body into a delivery sheath prior to maneuvering the expandable cannula and impeller system to the target site; and
    removing the delivery sheath from the impeller body and the expandable cannula at the target site.

14. The method of claim 12, wherein transitioning the catheter pump from the separated configuration to an operational configuration comprises operating an actuator coupled to the impeller system.

15. The method of claim 14, wherein the actuator comprises:
    an impeller anchor rotatably coupled to the impeller system, whereby at least an impeller shaft of the impeller system is rotatable relative to the impeller anchor and
    a cannula anchor coupled to the expandable cannula, and wherein operating the actuator comprises sliding the impeller anchor relative to the cannula anchor to translate the impeller anchor axially relative to the cannula anchor and transition the catheter pump between the separated configuration and the operational configuration.

16. The method of claim 15, wherein operating an actuator comprises manipulating a knob coupled to the actuator, wherein the knob is fixedly coupled to the impeller anchor and extends radially outward from the impeller anchor through an opening defined by the cannula anchor.

17. The method of claim 12, wherein transitioning the catheter pump from the separated configuration to the operational configuration comprises engaging a distal end of the expandable cannula with the bearing assembly of the impeller system.

18. The method of claim 12, further comprising operating the catheter pump by rotating the impeller body while the bearing assembly remains substantially stationary.

19. The method of claim 12, wherein the impeller body is positioned inside the expandable cannula in the operational configuration.

20. A catheter pump, comprising:
    an expandable cannula defining a blood flow channel and comprising an impeller blade zone, a single inlet zone including a flared portion that widens between a proximal end and a distal end to securely engage a portion of an impeller system; and
    the impeller system comprising an impeller body, the impeller system movable relative to the expandable cannula along a longitudinal axis of the catheter pump,
    wherein the catheter pump is selectively transitionable between a separated configuration in which the impeller body is axially spaced from the expandable cannula along the longitudinal axis, and an operational configuration in which the impeller body is positioned within the impeller blade zone of the expandable cannula and the portion of the impeller system is securely engaged with the flared portion of the expandable cannula, thereby securing the impeller system relative to the expandable cannula, and
    wherein when the catheter pump is in the separated configuration, the inlet zone includes the flared portion, such that the flared portion is not held open by a bearing assembly and such that the flared portion is sizeable and shapeable according to a size and a shape of the impeller body and the bearing assembly before the impeller body and the bearing assembly are received.

* * * * *